United States Patent [19]

Shigetoyo

[11] Patent Number: 4,860,488

[45] Date of Patent: Aug. 29, 1989

[54] VOLATILE INSECTICIDE EMITTER

[75] Inventor: Hiromi Shigetoyo, Tokyo, Japan

[73] Assignee: Nihon Naishi Co., Ltd., Japan

[21] Appl. No.: 65,935

[22] Filed: Jun. 23, 1987

[51] Int. Cl.⁴ ............................................. A01M 1/20
[52] U.S. Cl. ..................................... 43/129; 43/132.1
[58] Field of Search ....................... 43/125, 129, 132.1

[56] References Cited

U.S. PATENT DOCUMENTS

| | | | |
|---|---|---|---|
| 1,842,900 | 1/1932 | Ell | 422/124 |
| 2,510,126 | 6/1950 | Melcher et al. | 43/129 |
| 3,290,112 | 12/1966 | Gillenwater et al. | 43/129 |
| 3,793,763 | 2/1974 | Griffin et al. | 43/129 |
| 3,807,082 | 4/1974 | Hautmann et al. | 43/125 |
| 4,228,124 | 10/1980 | Kashihara et al. | 43/125 X |

FOREIGN PATENT DOCUMENTS 4925097 6/1974 Japan.

Primary Examiner—Nicholas P. Godici
Assistant Examiner—Carmine Cuda
Attorney, Agent, or Firm—Lucas & Just

[57] ABSTRACT

This invention discloses a volatile insecticide emitter having the construction wherein volatile insecticidal plates each formed by impregnating a plastic absorber with dimethyl dichlorovinylphosphate as an insecticidal component are juxtaposed in an inner space of a box-shaped container, an air filter is disposed at one of the air holes of the container communicating the inner space with the outside of the container and a motor fan is disposed at the other of the air holes so that the insecticide emitted inside the container is compulsively emitted outside the container.

3 Claims, 2 Drawing Sheets

VOLATILE INSECTICIDE EMITTER

BACKGROUND OF THE INVENTION

This invention relates to a volatile insecticide emitter for effectively getting rid of noxious insects such as flies, mosquitoes and particularly cockroaches by emitting an insecticide from the surface of an insecticidal plate impregnated with insecticidal components.

Emissible insecticidal plates have been used for getting rid of noxious insects such as flies, mosquitoes, cockroaches, etc by placing a single insecticidal plate B in a mesh bag C as shown in FIG. 5 and suspending the bag at a position higher than people, e.g. from a ceiling or a wall, in order to emit fine insecticidal particles into air and to exterminate the noxious insects at a predetermined concentration of insecticidal components for a predetermined effective period.

When the mesh bag storing therrein the insecticide is suspended and used, a zone having a predetermined insecticidal concentration is formed at an upper space of a room (e.g. kitchen) and flies and mosquitoes can be exterminated effectively at the upper space but cannot render an effective insecticidal effect for cockroaches that are active near the floor. To exterminate the cockroaches, therefore, the insecticidal plate must be disposed in an upper space near to the floor so as to form a zone having a predetermined insecticidal concentration. However, disposition of the insecticidal plate at such a portion is practically impossible amd the range of utilization of the insecticidal plate of this kind is unavoidably limited. The use of the suspension type insecticidal plate is not desirable from the aspect of appearance depending upon the position of use.

Furthermore, the predetermined effective period of the insecticidal plate is relatively long, and dust or the like is likely to attach to the surface of the plate B and reduces its emission ratio and hence, its insecticidal effect. If the dust or the like attaching to the surface of the insecticidal plate B is wiped off by paper or cloth, the insecticidal plate B can be used once again so long as its life remains, but such a cleaning work is troublesome in practice. Therefore, even during the effective period, the insecticidal plate B is often discarded uneconomically. The emission capacity of the insecticidal plate drops below a predetermined temperature (17° C.) and its insecticidal effect drops, though the noxious insects are active in that temperature range.

SUMMARY OF THE INVENTION

In view of the problems of the prior art described above, the present invention is directed to protect an insecticidal plate from its surface contamination, to consume effectively and economically its insecticide for a predetermined period, to make the insecticidal plate easier to use without limitation of its use, to expand the range of its utilization and to improve the extermination effect of noxious insects by forming easily and effectively a concentration zone of insecticidal components.

In order to accomplish the objects described above, the present invention provides a volatile insecticide emitter having the construction wherein an insecticidal plate capable of emitting insecticidal components from its surface is stored and fixed in an inner space of a container which is partitioned from outside and has a predetermined shape, a motor fan is fixed at an air hole of the container communicating the inner space and with the outside of the container in an emitting direction and an air filter is disposed at an inlet of an air stream.

DESCRIPTION OF THE PREFERRED EMBODIMENT

Hereinafter, the present invention will be described in detail with reference to the accompanying drawings.

Figure 1:
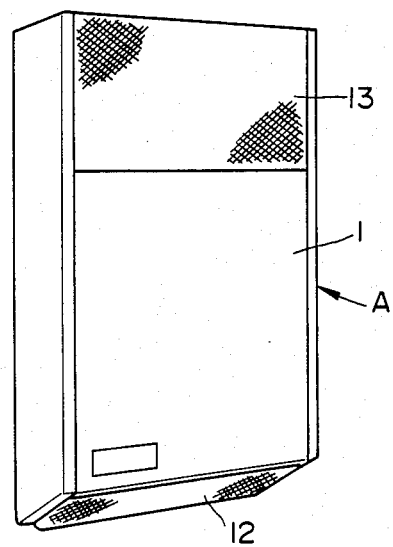
FIG. 1 is a perspective view of a volatile insecticide emitter.
Figure 2:
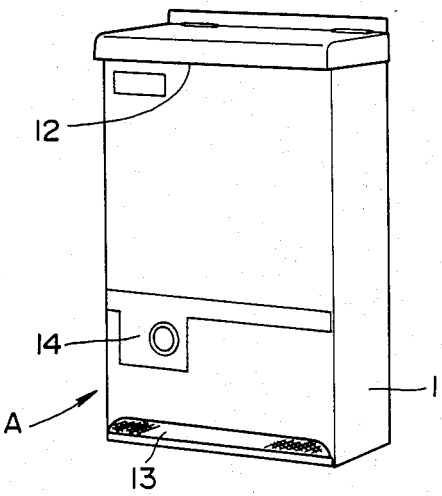
FIG. 2 is a perspective view of a different model of the volatile insecticide emitter.

FIG. 1 is a perspective view showing the overall appearance of an insecticide emitter, which is an ordinary model used for getting rid of noxious insects in general such as flies and mosquitoes, while FIG. 2 shows a specific model for exterminating cockroaches.

In FIGS. 1 and 2, reference numeral 12 represents an air inflow port and reference numeral 13 represents an insecticide emission port.

In FIG. 2, reference numeral 14 represents an external operation unit for operating a motor fan and a heater that are disposed inside the emitter frame.

Figure 3:
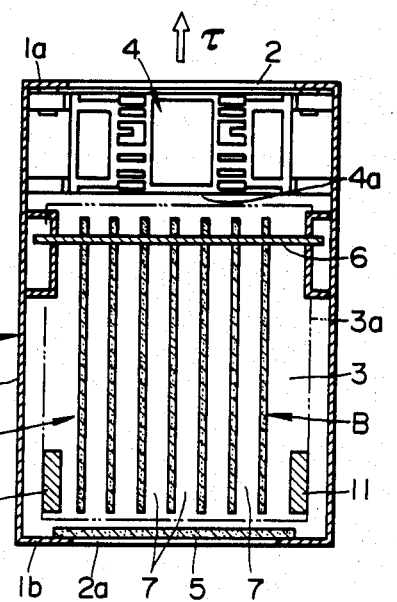
FIG. 3 is a longitudinal sectional view of the principal portions of the volatile insecticidal emitter.

FIG. 3 is a longitudinal sectional view of the principal portion of the insecticide emitter A. In the drawing, reference numeral 1 represents a container which is partitioned from outside and has a box-like shape or other shape. When this container 1 is used as a vertical type, upper and lower air holes 2 and 2a are bored on upper and lower walls 1a and 1b, respectively, in order to communicate the inner space 3 of the container with the outside. Reference numeral 4 represents a motor fan, which is fixed to the container in such a manner that its suction port 4a faces the inner space 3 when wind is to be generated in a direction represented by symbol τ, that is, for upward blow, and insecticidal components can be emitted outward through the upper air hole 2. When the wind is to be generated towards the lower air hole 2a, that is, for downward blow, the motor fan is disposed in the same fitting posture but on the side of the lower air hole.

On the other hand, the motor fan 4 is disposed from time to time in such a manner that its suction port 4a faces outside as shown in FIG. 3. In this case, downward blow and emission are made from the lower air hole 2a. Reference numeral 5 represents an air filter. When the lower air hole 2a is used as the air inflow path, the air filter 5 is fixed to the lower air hole 2a so as to remove any floating matters such as dust that are likely to flow into the inner space 3. As described above, when the direction of the wind is to be formed in the direction opposite to symbol τ, the air filter 5 is fixed to the upper air hole 2 that faces the suction port 4a of the motor fan 4. Symbol B represents an insecticidal plate, which is disposed in the inner space between the motor fan 4 and the air filter 5. A support rod 6 penetrating through the inner space 3 in an orthogonal direction to the direction of the wind is fixed to the side walls of the container 1 and one or a plurality of insecticidal plates B are suspended therefrom. When a plurality of insecticidal plate B are used, predetermined spacings are secured between their adjacent surfaces as paths for the emitted insecticide.

Figure 4:
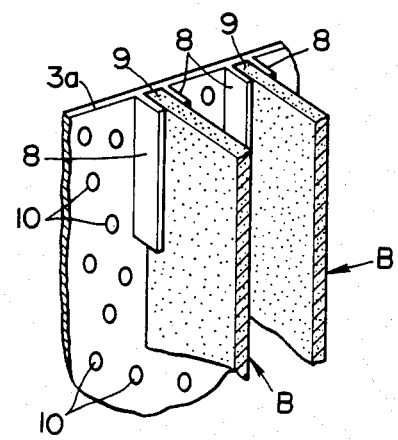
FIG. 4 is a partial perspective view when an insecticidal plate is fitted into an inner container.
Figure 5:
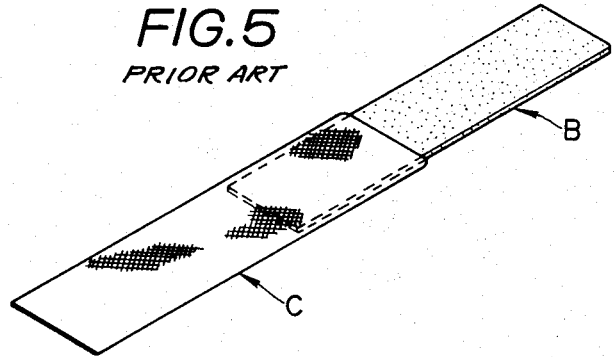
FIG. 5 is a perspective view of a conventional insecticidal emitter.

The inner space 3 can be modified to an inner container 3a (chemical case) which is partitioned therearound inside the container 1 as shown in FIG. 4. In this case, each insecticidal plate B is slid and fitted and fixed between guide grooves 9 that are formed between right and left guide plates 8 projecting from the inner walls of the inner container 3a in such a manner as to oppose each other. Reference numeral 10 represents a large number of emission ports that are bored on the inner wall 3a, which are disposed whenever necessary. Reference numeral 11 represents a heater, which is disposed inside the inner space 3. The heater 11 and the motor fan 4 may have a remote control operation outside the container or may be operated automatically by means of a time limiting device or a thermodevice that is built in each of the heater 11 and the motor fan 4.

Since cockroaches and flies are nocturnal, it will be economical if the insecticide emitter are operated for a predetermined necessary period and the insecticidal components can be preserved in the inner space by so doing. These noxious insects become extremely inactive below a predetermined temperature, but if the insecticidal effect drops due to the drop of the emission ratio even within the active temperature range of these noxious insects, a suitable temperature range for emission is always kept by the heater. Incidentally, dimethyl dichlorovinylphosphate is used as the insecticidal component of the insecticidal plate and a plastic absorber is impregnated with this insecticidal components. Additionally, the container 1 is ordinarily equipped with fixing means for fixing it on the wall or the like.

As described above, since the insecticidal plate is disposed and fixed in the inner space between the motor fan and the air filter in the insecticide emitter in accordance with the present invention, it becomes possible to prevent surface contamination of the insecticidal plate and to fully use the insecticidal plate efficiently and economically during its effective period. Even when a plurality or a large number of insecticidal plates are used, the insecticide emitter of the present invention has good appearance and can expand the range of its utilization. The motor fan can form reliably and safely a predetermined concentration zone of the insecticidal component in accordance with the active zone of noxious insects and can extremely improve and expand the insecticidal effect and the range of utilization. If a timer or a thermo-device is used, the insecticidal component can be emitted automatically only in the active period of nocturnal noxious insects and the insecticidal plate can thus be used more economically. Furthermore, the insecticidal emitter of the invention can exterminate noxious insects within their active range even at a low temperature without causing the drop of the emission ratio.

What is claimed is:

1. An insecticide emitter comprising:
   a container, said container having an air inflow port and an insecticide emission port;
   an air filter covering said air inflow port for filtering the inflowing air;
   a plurality of insecticidal plates each formed by impregnating a plastic absorbent material with dimethyl dichlorovinylphosphate as an insecticidal component, said plates being juxtapositioned with one another and having a set spacing between each of said plates, said plates positioned inside said container;
   a heater for only heating the inside of said container when the temperature is less than or equal to about 17° C.; and
   a motorized fan for drawing air in through said inlet port, over said plates and expelling said air through said insecticide emission port.

2. The insecticide emitter of in claim 1 wherein said inner space is a chemical case stored removably inside said box-shaped container.

3. The insecticide emitter of claim 1 further comprising a timer to select the period of time when said insecticide emitter is on.

* * * * *